United States Patent [19]

Ward

[11] Patent Number: 4,753,232

[45] Date of Patent: Jun. 28, 1988

[54] ADHESIVE WOUND DRESSINGS

[75] Inventor: William J. Ward, Hull, United Kingdom

[73] Assignee: Smith & Nephew Associated Companies p.l.c., United Kingdom

[21] Appl. No.: 730,292

[22] Filed: May 3, 1985

[30] Foreign Application Priority Data

May 3, 1984 [GB] United Kingdom ............... 8411368
May 23, 1984 [GB] United Kingdom ............... 8413231

[51] Int. Cl.$^4$ .......................................... A61L 15/00
[52] U.S. Cl. ............................................... 128/156
[58] Field of Search ................................... 128/156

[56] References Cited

U.S. PATENT DOCUMENTS

| 3,927,669 | 12/1975 | Glatt . | |
| 4,265,234 | 5/1981 | Schaar | 128/156 |
| 4,344,426 | 8/1982 | Caumont | 128/156 |
| 4,372,303 | 2/1983 | Grossmann et al. . | |
| 4,374,520 | 2/1983 | Grossmann et al. . | |
| 4,381,611 | 5/1983 | Wishman | 128/156 |
| 4,413,621 | 11/1983 | McCracken et al. . | |
| 4,534,354 | 8/1988 | Bonner | 128/156 |

FOREIGN PATENT DOCUMENTS

| 0051935 | 5/1982 | European Pat. Off. . |
| 0066899 | 12/1982 | European Pat. Off. . |
| 0081987 | 6/1983 | European Pat. Off. . |
| 0081989 | 6/1983 | European Pat. Off. . |
| 0081990 | 6/1983 | European Pat. Off. . |
| 0117632 | 5/1984 | European Pat. Off. . |
| 0120570 | 10/1984 | European Pat. Off. . |
| 2120104 | 11/1983 | United Kingdom . |

Primary Examiner—Gregory E. McNeill
Attorney, Agent, or Firm—Jacobs & Jacobs

[57] ABSTRACT

An adhesive wound dressing which comprises a flexible polymer film having an adhesive surface and a non-adhesive surface on the opposite side, a removable protector over the adhesive surface and a detachable handle along an edge margin of the polymer film is described. The handle is used to facilitate handling of the film during application of the dressing and is formed from a tearable material so that it can be removed by tearing without disturbing the applied dressing. In a second described embodiment the tearable handle carries an adhesive coating so that the user has the option of removing the handle or adhering it to the skin of the patient.

19 Claims, 3 Drawing Sheets

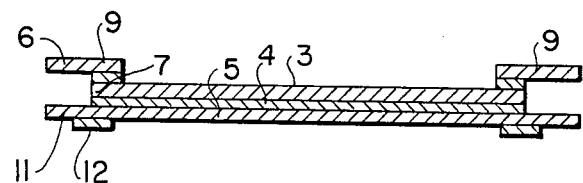
Fig. 5
Fig. 6
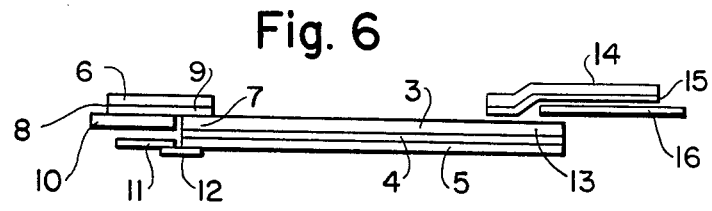
Fig. 7
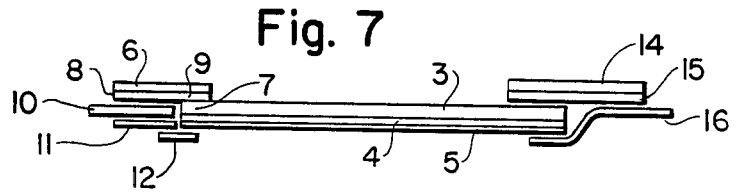
Fig. 8
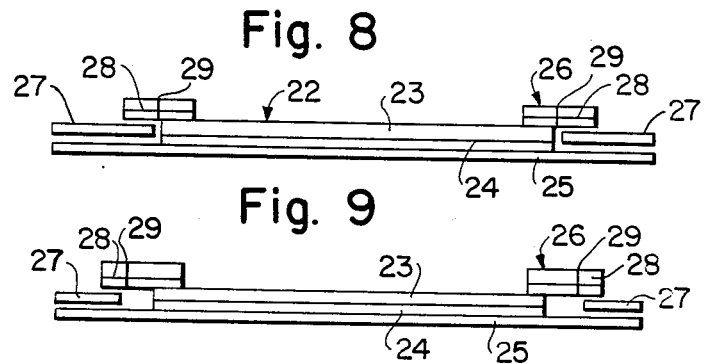
Fig. 9

ADHESIVE WOUND DRESSINGS

The present invention relates to adhesive wound dressings and processes for their manufacture and use.

Conventional adhesive wound dressings usually comprise an adhesive coated sheet with a removable protector over the adhesive coating. The application of these wound dressings to a patient can be achieved by removing the protector from the adhesive sheet and adhering the sheet to a patient's skin at the wound site. Such dressings must be sufficiently conformable to allow the dressing to be worn in comfort by the patient and not to become dislodged by movement of the patient. The sheet used in these dressings is conventionally a thin elastomeric film. When coated with adhesive this flexible film can be difficult to handle during its application to a patient resulting in the dressing creasing or puckering or otherwise self-adhering. In one way of overcoming this problem the flexible adhesive coated sheet of such conformable dressings can have one or more non-adhesive handles at an edge or edges thereof to facilitate handling of the sheet. A highly conformable adhesive wound dressing of this type is known as "OpSite" (Trade mark) marketed by T. J. Smith & Nephew Limited. The "OpSite" wound dressing, which comprises a flexible polyurethane backing, has a pair of plastics strip handles adhered to opposed edges of the adhesive coated sheet to provide non-adhesive surfaces for handling the sheet. After the application of such adhesive wound dressings to a patient the non-adhesive handles are usually removed by cutting from the adhered sheet. Such a method of removal, however, can leave the applied dressing with "lifted" and unevenly cut or ragged edges which can self-adhere or roll up and cause the dressing to progressively "lift off" in use. European Patent Application No. 0081987 and U.S. Pat. No. 4,413,621 disclose an adhesive wound dressing which comprises a flexible adhesive coated sheet having a pair of non-adhesive handles, formed of the same material as the flexible sheet, adjacent to perforation lines on opposed side edges of the sheet. These handles can be detached from the sheet, after application of the dressing, by separating along the perforation lines. Although the provision of perforations in the sheet allows the handles of such a wound dressing to be removed or detached more easily than the handles of conventional adhesive wound dressings, the removal of the handles still employs a force which can result in the lifting of the edges of dressing. Furthermore, the edges of the applied dressing, which result from detachment along the perforation lines, are unlikely to be even. Trauma can also be caused to the wound when the edges are pulled during removal of the handles.

United Kingdom Patent Application No. 2120104 describes an adhesive wound dressing and delivery system which comprises a laminate of a semi-rigid non-flexible delivery means layer adhered by a pressure sensitive adhesive to an intermediate wound dressing layer having on the opposite surface to the delivery means a further pressure sensitive adhesive layer covered by a protector. One edge of the wound dressing layer may carry a perforated line and the wound dressing layer in this area may be reinforced by one or more strips. In use after adhering the wound dressing layer at the wound site first the delivery means and then the non-adhesive handle must be removed. The handle is removed along the perforated line which means that the dressing layer is effected by removing the handle which may cause lifting or other disturbance of this layer along its torn edge.

European Patent Application No. 66899 describes a delivery system for an adhesive wound dressing in which a film sheet carrier supports an adhesive coated wound dressing layer. When the dressing is in place the carrier is removed. A non-adhesive tab strip is permanently adhered to one edge of the wound dressing and remains in place after the dressing has been adhered to the patient. The tab forms a non-detachable, non-adherent handle which could lead to the dressing lifting as a result of movement by the patient.

U.S. Pat. Nos. 4,372,303 and 4,374,520 each describe a system for bandaging a patient in which a stiff handling means is applied to a flexible, adhesive bandage prior to application of the bandage to a patient. The handling means maintains the bandage in a generally flat configuration during application but because of its stiffness must be removed once the bandage is in place. The removal may cause disturbance to the edge of the applied dressing and may result in the edges self adhering or rolling up so causing the dressing to "lift off" in use.

European Patent Application No. 51935 describes a device in the form of an adhesive dressing comprising a thin, conformable, adhesive-coated film which has attached to the surface opposite the adhesive layer a supporting releasable layer. After the dressing has been placed on the skin the releasable layer is removed. The removal of the release layer from contact with the applied dressing may cause disturbance of the dressing by lifting its edges.

European Patent Application No. 81989 describes an adhesive dressing comprising an adhesive coated transparent polymeric film and a release sheet covering the adhesive coating. A perforation line is present in the film spaced inwardly from the periphery of the film. A cut line is present in the release sheet spaced inwardly from the periphery of the sheet. In use the central portion of the release sheet is removed by tearing along the cut line, the dressing is adhered to the skin using the remaining release portion as a handling means and finally the remaining release sheet and the periphery of the film are removed by tearing along the perforated line. This will leave an edge to the dressing which is unlikely to be even and which may cause the edge of the dressing to roll up in use.

European Patent Application No. 81990 describes an adhesive dressing comprising a transparent, continuous, adhesive coated film with a fibrous backing material secured to the side of the film opposite to the adhesive layer. The fabric backing may be removed from the film after the dressing has been placed on the skin of the patient. The force required to remove the fabric backing from contact with the applied dressing may cause disturbance to the dressing.

European Patent Application No. 117632 discloses a surgical dressing in the form of a thin polymeric film having one surface coated with a pressure sensitive adhesive, the adhesive layer is covered with a removable release sheet comprising three sections. In use the centre portion of the release sheet is first removed and the dressing adhesively secured to the patient. The remaining two sections of the release sheet are then removed. This application does not suggest the use of tearable handles.

European Patent Application No. 120570 describes a wound dressing having a protective sheet in releasable contact with the adhesive of an adhesive coated backing sheet. There is a release retarding means along one edge or pair of opposed edges so that a greater force is required to separate the backing sheet from the protective sheet at the edges than in the central portion of the dressing. In use the central portion of the dressing is exposed and adhered to the patient using the protective sheet which is still joined at its edges to the backing sheet as a manipulation means. When the centre of the dressing is in place the protective sheet is removed by tugging it away from the backing sheet. The force required to remove the parts of the protective sheet may cause the applied dressing to become disturbed.

U.S. Pat. No. 3,927,669 describes a bandage comprising a hygroscopic pad which has adhered to one surface an adhesive coated strip like element for affixing the bandage to the body. The strip-like element may have a line of perforations whereby the length of the bandage may be shortened by tearing along the perforations. That patent does not disclose or suggest that this would be applicable to membrane dressings of the type envisaged in the present invention.

U.S. Pat. No. 4,122,552 describes a disposable undergarment having a plurality of bands of strip-away material whereby their selective removal provides garments of varying size. That patent does not disclose or suggest that this system would be applicable to membrane dressings of the type envisaged in the present invention.

It has now been found that by using a handle which is tearable as an aid to positioning the dressing on a patient, a portion of the handle may be subsequently removed by tearing through the handle without having to tear through the wound dressing layer and so disturb it. Further if the handle is also coated with a adhesive the user has an option of allowing the handle to remain in place by adhering it to the skin or removing part of it and adhering any residual handle to the skin to avoid leaving any loose flaps. A particular advantage of an adhesive handle is that it may be adhered to the patient without having to remove the protector over the adhesive surface of the dressing. The adhered handle may then serve as an anchor point so that both hands are free to manoeuvre the dressing into position and to remove the protector from the dressing prior to adhering it to the skin. This technique of applying the dressing also prevents the dressing being applied under excessive tension. Further the wound dressings of the present invention do not require the presence of an additional delivery means although such may be included if desired.

Accordingly the present invention provides an adhesive wound dressing which comprises a flexible sheet having both an adhesive surface and a non-adhesive surface on the opposite side thereof, a detachable handle at an edge of the sheet to facilitate handling of the sheet and a removable protector over the adhesive surface of the sheet, characterised in that the handle is adhered along an edge margin to an edge margin of the flexible sheet and which handle is formed from a tearable material to allow the handle to be detached from the sheet.

In a preferred aspect the handle will have an adhesive coat on one surface so that it may be adhered to the skin of patient when the dressing is in place. In this aspect the adhesive surface of the handle which is not serving to adhere the handle to the flexible sheet will be covered by a protector prior to use.

From the foregoing it is clear that the adhesive surface on the handle and the adhesive surface on the flexible sheet will be on the same side so that both may be adhered to the body.

Thus in a second aspect the present invention provides an adhesive wound dressing which comprises a flexible polymer film having both an adhesive surface and a non-adhesive surface on the opposite side thereof, a detachable handle at an edge of the sheet to facilitate handling of the film and a removable protector over the adhesive surface of the film, characterised in that the handle is coated on one surface with an adhesive and is adhered along an edge margin to an edge margin of the flexible film, the remaining area of adhesive of the handle being covered by a removable protector and which handle is formed from a tearable material to allow the handle to be detached from the film.

The adhesive dressings of the present invention are suitable for application to wounds that, is to lesions of the skin, which have been caused either by physical trauma, for example burns, or by surgical intervention, for example post-operative sites, skin donor sites and particularly intravenous sites where a catheter or a cannula has been used to gain access to the venous system of a patient on a long term basis all of which uses require that the site must be protected from infection.

By 'tearable material' is meant material which may be tearable per se or has been adapted to be tearable, for example by edge notching, embossing, orientation or fibrillation. Generally the tear will be a straight line tear and may be initiated by means of the fingers, thus favourably the material is finger tearable.

The handle used in the wound dressings of the invention can suitably be a film, sheet or web. The handle is preferably stiffer than the flexible adhesive coated film so that it provides support to it during its application to the patient. Suitable handles can be made of a wide variety of materials including paper, non-woven fabric, woven fabric and films, sheets or webs of polymers including polypropylene, polyethylene, copolymers thereof and blends thereof and blends including polystyrene, polyester and polyvinyl chloride. The handle will be either tearable per se like paper or some nonwoven and woven fabrics or be adapted to be tearable for example, by edge notching or by embossing or by orienting of a film so as to make it tearable in a preferred direction. Favourably the handle will be adapted to be capable of being torn in a substantially straight line.

Particularly apt materials for forming the handle include paper, porous polyvinyl chloride sheet such as that sometimes known as Porvic (Trade mark) which is conventionally used in the manufacture of first aid dressings, non-woven fabric such as spun-bonded polyester fabric (Sontara, Trade mark), polyester film (Melinex, Trade mark), woven acrylic fabric, embossed films of low or high density polyethylene or polypropylene, integral nets formed by the fibrillation of embossed films and oriented polypropylene films.

Particularly favoured materials for forming the handle are embossed films particularly those which are melt embossed on one or both surfaces with a series of grooves which delineate the preferred tear direction. Such melt embossed films are described in for example British Patents Nos. 1110051, 1267031, 1495151 and 1496786. Use of such materials gives rise to particularly easily removable handles.

However, particularly preferred materials for forming the handle are integral nets particularly those formed by the fibrillation of thermoplastic embossed polyolefin films comprising low and high density polyethylene, polypropylene or copolymers or blends thereof or blends of polyolefin with polystyrene. Such nets which have been adapted to tear in a preferred direction by orientation of the polymer forming them are described in British Patents Nos. 1495151 and 1531715.

A particularly preferred net is formed from a blend of polymers in which a high density medically approved polyethylene forms the major component, for example 5 parts by weight and a high impact polystyrene forms the minor component, for example 1 part. An embossed film of the blend is formed by passing a mixture of the polymers in a molten state through the nip between two rollers, one roller having a pattern of axial grooves on its circumferential surface and the other roller having a pattern of cavities which give rise to raised areas or bosses on one side of the film. Suitably the cavities are hexagonal cavities. The number of grooves per inch may be in the range 50 to 500 and the number of raised areas or bosses 100 to 10. The number of grooves per inch is suitably an integral number of bosses per inch and is 2 to 20 times the number of bosses. The film is then stretched in the transverse direction by at least 50% to fibrillate the areas between the bosses to form a net which is tearable in two directions sustantially at right angles to each other.

An integral net is a net with strands and junctures which have been formed integrally during manufacture.

Since in one method of use the handle may be adhered to the skin rather than being detached, it is preferred that the handle when coated with adhesive should have a moisture vapour permeability (mvp) of at least 300 $gm^{-2}24h^{-1}$ at 37° and 100% to 10% relative humidity when measured by the Payne Cup Method. More suitably the adhesive coated handles should have an mvp of at least 500 $gm^{-2}24h^{-1}$ and preferably should be at least 700 $gm^{-2}24h^{-1}$. The handle may then be safely adhered to the skin without the risk of causing maceration to the underlying normal healthy skin. The method used for measuring moisture vapour permeability is described in European Patent Application No. 107315 at page 52.

An adhesive such as one of those described in British Patent No. 1280631 or European Patent Application No. 35399 may be spread onto the smooth surface of the net as hereinbefore described, that is the one which was embossed with the series of grooves. A particularly suitable adhesive is an acrylate ester copolymer adhesive formed from the polymerisation of 47 parts 2-ethylhexyl acrylate, 47 parts butyl acrylate and 6 parts acrylic acid. This combination of net and adhesive gives a tape of both high moisture vapour permeability (mvp) and tearability which is particularly apt for the dressings of the present invention. If the adhesive layer is continuous the mvp is approximately 800 $gm^{-2}24hr^{-1}$ and if the adhesive layer is porous the mvp may be as high as 8000 $gm^{-2}24hr^{-1}$, when measured at 37° C. and 100% to 10% relative humidity.

Suitably the handle will be from 1.0 cm to 4.0 cm in width and preferably 1.5 to 2.5 cm in width, for example 1.8 cm, 2.0 cm or 2.2 cm in width. The width of the margin of the handle which is adhered to the edge margin of the flexible sheet is then suitably 0.15 to 0.5 cm and is preferably 0.2 to 0.3 cm.

In another favoured embodiment the handle is formed from a plastics film handle portion and an adhesive tape. The handle portion may or may not have an adhesive layer on one surface thereof. The handle portion is positioned abutting the flexible film. The adhesive tape is placed over an edge margin of the flexible film and at least an edge margin of the handle portion so as to attach the flexible film and the handle portion. A line of perforations is present through the adhesive tape. The line of perforations is positioned over the joint between the flexible film and the handle portion so that neither the flexible film nor handle portion is perforated, but separation of the handle is achieved by tearing along the perforated line. The adhesive tape may be formed from a paper coated on one surface with a pressure sensitive adhesive. Both the adhesive tape and handle portion may also be coloured for example green. If it is required to adhesive coat the handle portion, the adhesive surface will be covered by a release coat.

In an alternative construction the handle portion may be offset from the flexible film so that a wider tape is required to attach the handle portion to the flexible film. The exposed adhesive surface of the tape is covered by the protector which also covers the adhesive surface of the flexible film. The line of perforations is so positioned so as to allow the residual adhesive tape on the flexible film to be adhered to the skin after removal of the handle thereby providing a neat edge to the dressing.

In one embodiment of the invention the adhesive wound dressings will have only one handle. Such dressings are conventionally preferred for use at intravenous sites.

In a second embodiment of the invention the adhesive wound dressing will have a handle at each of two opposite sides of the wound dressing. Such dressings are conventionally preferred for use on wounds caused by physical trauma or surgical invention though they may equally well be used in conjunction with indwelling catheters or cannulae.

The flexible polymer film which have both an adhesive coated surface and a non-adhesive coated surface on the opposite side of the film may comprise any of the flexible polymer films conventionally used for surgical or wound dressings. The sheet material is a polymer film and most preferably a film of elastomer. Preferably the flexible film is moisture vapour permeable and bacteria proof. In addition it is most convenient to employ a transparent material. Favoured moisture vapour permeable, liquid water impermeable, flexible sheets will have a moisture vapour permeability of at least 300 $gm^{-2}24h^{-1}$ at 37° C. at a relative humidity difference of 100% to 10%, more suitably at least 400 $gm^{-2}24h^{-1}$, preferably at least 500 $gm^{-2}24h^{-1}$ and most preferably at least 700 $gm^{-2}24hr^{-1}$.

Suitable flexible films for use in the invention are described in British Patent No. 1280631 and European Patent Application No. 51935. Favoured flexible polymeric films include those formed from a polyether or polyester polyurethane. Suitable polvether polyurethanes are described in U.S. Pat. No. 2,899,411, and suitable polyester polyurethanes are described in U.S. Pat. No. 2,871,218. Suitable polyether and polyester polyurethanes include those known as Estanes (Trade mark, available from B.F. Goodrich Corp.). Preferred polyurethanes are available as Estanes 5701, 5702, 5703, 5714F and 580201. A second particularly favoured flexible film may be formed from an elastomeric polyether polyester. Preferred polyether polyesters include Hytrel 4056 (Trade mark, available from E.I. du Pont de Nemours & Co.).

Suitably the thickness of the flexible films used in the invention will be from 9 to 80 microns, more suitably 15 to 50 microns and preferably 20 to 40 microns for example 25 microns, 30 microns or 35 mircrons.

A second favoured form of adhesive wound dressing to which tearable handles may be applied is described in European Patent Application No. 107915.

That application describes a moisture vapour permeable adhesive surgical dressing comprising a continuous film which has a moisture vapour permeability which is greater when in contact with water than when not in contact with water and which film is attached to a water transmitting film so as to form a sealed portion into which exudate may pass from an exuding wound, said water transmitting layer being interrupted in at least the area within the sealed portion and which water transmitting layer comprises a backing layer and an adhesive layer on the side remote from the continuous film which is suitable for adhering the dressing to the skin. Such a dressing is suitable for attachment of handles formed from tearable material as hereinbefore described. Aptly a margin at the edge of the handle will be attached to a margin of the continuous moisture vapour permeable sheet. Attachment may be by any conventional means but use of an adhesive is preferred. The handle is aptly attached on the surface remote from that sealed to the water transmitting film though if desired the handle could be attached so that its margin was sealed between the moisture vapour permeable film and the water transmitting film.

A particularly preferred adhesive wound dressing has a continuous film formed from a hydrophilic polyurethane, a water transmitting film formed from an adhesive coated low moisture vapour permeable polymer film, such as a styrene-butadiene-styrene polymer, which has been apertured by means of a plurality of slits and in which a layer of a water transmitting film of a non-woven fabric, such as a spun-bonded polypropylene is present between the continuous film and the water transmitting film.

When present the adhesive layer on the handle used in dressings of the present invention may be a continuous spread or a non-continuous spread, for example pattern spread, a microporous layer or a porous layer.

Suitably the adhesive layer will be 15 to 65 microns thick, preferably is 20 to 40 microns thick, for example 25, 30 or 35 microns thick. Such adhesive layers will generally have a weight of adhesive per unit area of 10 to 75 $gm^{-2}$, more usually 15 to 65 $gm^{-2}$ and preferably 26 to 40 $gm^{-2}$.

Suitable adhesives include those which are described in British Patent No. 1280631 and European Patent Applications Nos. 51935, 35399. Preferably, the adhesive is a polyvinyl ether adhesive such as polyvinyl ethyl ether adhesive or an acrylate adhesive such as an acrylic ester adhesive. Examples of the latter include acrylate ester copolymers which contain hydrophilic groups, for example a copolymer of 47 parts by weight butyl acrylate, 47 parts by weight 2-ethylhexyl acrylate and 6 parts by weight acrylic acid.

If the adhesive layer is a continuous spread then it is prepared from a material which when spread on a handle or flexible sheet will allow the adhesive coated material to have a moisture vapour permeability (mvp) of at least 300 $gm^{-2}24h^{-1}$ at 37° C. and 100% to 10% relative humidity when measured by the Payne Cup Method, more favourably the mvp will be at least 400 $gm^{-2}24h^{-1}$, most favourably at least 500 $gm^{-2}24h^{-1}$ and preferably at least 700 $gm^{-2}24h^{-1}$.

A similar adhesive may be used on the flexible polymer film present in the wound dressings of this invention and will be applied in a similar continuous or discontinuous manner and suitably will give the moisture vapour permeabilities hereinbefore described.

Since the adhesive wound dressings of the present invention are to be adhered to normal healthy skin then to avoid maceration of that skin then it is arranged that the adhesive wound dressing will have a moisture vapour permeability of at least 300 $gm^{-2}24h^{-1}$ at 37° C. and 100% to 10% relative humidity, more suitably will be at least 500 $gm^{-2}24h^{-1}$ and preferably will be at least 700 $gm^{-2}24h^{-1}$.

In the dressings of the present invention, the handle and the flexible sheet overlap at their edge margins. Irrespective of whether the rest of the handle is removed or adhered to the skin this overlap area will remain on the dressing and will by virtue of the adhesive on the flexible sheet be adhered to the skin. In order to avoid maceration of the underlying skin in this overlap area, the dressing in this area will favourably have an MVP of at least 300$gm^{-2}24hr^{-1}$ at 37° C. and 100% to 10% relative humidity difference, more favourably the MVP will be at least 500$gm^{-2}24hr^{-1}$ and preferably be at least 700$gm^{-2}24hr^{-1}$.

Suitable protectors include silicone release coated papers and plastics coated papers and release coated films such as silicone coated polyethylene. A favoured release protector is a silicone release/polyethylene coated paper known as Steralease No. 15 (Trade mark, available from Sterling Coated Paper Limited).

The adhesive wound dressing of the invention will usually have a rectangular shape. Suitable wound dressings have a size of 8 cm×8 cm to 20 cm×20 cm for example 10 cm×10 cm, 10 cm×15 cm, 15 cm×15 cm, etc.

The adhesive wound dressing of the invention is preferably sterile. The adhesive wound dressing of the invention is advantageously provided within a bacteria proof pack such as a sealed aluminium foil or paper/plastics film pouch. Sterilization of the dressing can be carried out by a conventional sterilizing method such as ethylene oxide, electron or gamma radiation.

In another aspect the invention provides a process of making an adhesive wound dressing of the invention which comprises attaching the edge margin of a handle to an edge margin of a flexible adhesive coated film which handle is formed from a tearable material whereby a portion of the handle may be detached from the film.

Suitable adhesive coated films and handles for use in the process of the invention are described hereinbefore in relation to the adhesive wound dressing of the invention.

The flexible film may be formed by casting or extrusion onto a support film, usually the non-release surface of a conventional release paper or polymer. The adhesive layer may be formed by casting or transfer coating onto the surface of the flexible film. The adhesive surface of the flexible film may then be transferred onto the release surface of the support film. The three layer laminate is then cut into a strip having the width of the required dressing.

The handles when adhesive may be formed by transfer coating an adhesive layer on a release paper onto the material forming the handle. This may then be cut into a strip of the appropriate width and attached to the edge of the flexible film.

The process of the invention may be carried out as a continuous process using continuous lengths of the flexible adhesive film and handles. Dressings of suitable size can then be made by cutting across the formed strips. In a process for making wound dressings which have a pair of handles at opposed side edges, the handles may be attached in consecutive or preferably simultaneous operation.

The preferred embodiments of the dressings of the invention will be described by way of example and with reference to the drawings in which:

FIG. 5 is a cross-sectional view of an adhesive wound dressing in which the handles do not carry an adhesive.

FIGS. 6 to 9 show cross-sections through alternate embodiments of adhesive wound dressings of the present invention.

Figure 1:
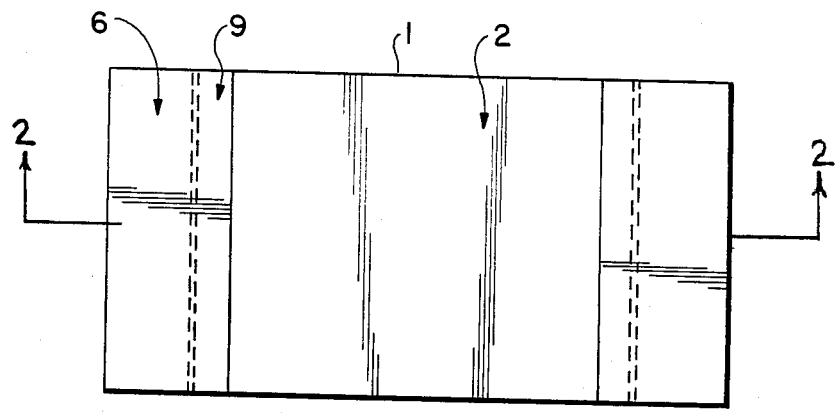
FIG. 1 is a plan view of an adhesive wound dressing of the invention.
Figure 2:
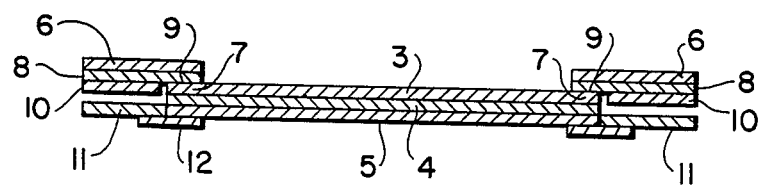
FIG. 2 is a cross-sectional view of the dressing along line 2—2 of FIG. 1.

FIGS. 1 and 2 show an adhesive wound dressing (1) which is of rectangular shape. The dressing comprises a flexible adhesive coated film (2) consisting of a flexible backing film (3) and an adhesive coating (4) which is covered by a protector (5). The adhesive wound dressing (1) has a pair of handles (6) at opposed side edge margins (7) of the flexible film (2). The handles (6) are coated with a layer of adhesive (8) so that the edge margins (9) of the handles (6) are attached to the edge margins (7) of the film (2) by means of a portion of this adhesive coating (8). The remainder of the adhesive surfaces on the handles (6) are covered with removable protectors (10). The protector (5) which covers the adhesive coating (4) may be extended to provide strips (11) which aid in removal of the protector from the adhesive wound dressing, by adhering the strips (11) using tabs (12).

Figure 3:
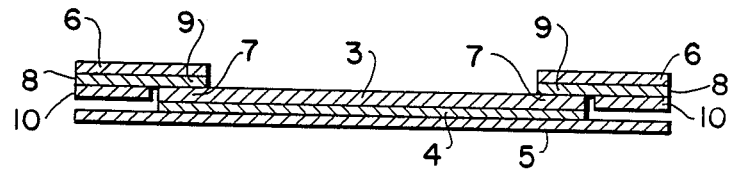
FIG. 3 is a cross-sectional view of an alternative embodiment of the present invention.

FIG. 3 shows an alternative adhesive wound dressing in which the protector (5) is formed of one piece which extends beyond the edges of the adhesive coated film (2) so that the extending pieces provide an aid to removal of the protector.

Figure 4:
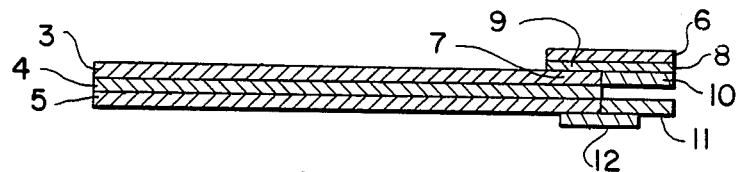
FIG. 4 is a cross-sectional view of an adhesive wound dressing which has only one handle.

FIG. 4 shows an adhesive wound dressing in which only one adhesive handle is present. Such dressings are used at intravenous sites.

FIG. 5 shows an adhesive wound dressing in which the handles are essentially non-adherent, being coated with adhesive only at their margins (9) where they are adhered to the margin of the flexible film.

FIG. 6 shows a further embodiment of an adhesive dressing of present invention in which the adhesive wound dressing (1) is formed from the conventional three layers comprising a flexible film (3) having on one surface a pressure sensitive adhesive layer (4) and a protector (5). One edge of the dressing has a handle (6) coated with a layer of adhesive (8) so that the edge margin (9) of the handle (6) can be attached to the edge margin (7) of the film (2). The remainder of the adhesive layer (8) is covered with a removable protector (10). At this edge, the protector (5) may be extended to provide a strip (11) which aids in the removal of the protector (5) from the adhesive wound dressing (1). The extra strip (11) is adhered to the protector (5) using adhesive-coated tab strip (12). The other edge of the dressing has adhered to its margin (13), an adhesive coated handle of a tearable material (14, 15). The protector (16) which covers the adhesive surface (15) of the handle (14) overlaps into the non-adhesive surface of the flexible film (3). In use the protector (16) is removed from the handle and the adhesive surface of the handle adhered to the patient to form an anchorage point for the dressing. The dressing is then positioned over the wound site and the protector (5) removed. The other handle is used to prevent both contamination of the exposed adhesive surface of the dressing and to prevent the dressing from wrinkling during the application process. When the dressing has been adhered to the skin, then the remaining handle may be removed or adhered to the patient.

FIG. 7 shows an embodiment of the adhesive dressing of the present invention similar to that described in FIG. 6 except that the protector (16) overlaps onto protector (5) of the wound dressing layer. In this embodiment the handle (14) is adhered to the skin of the patient prior to removal of the protector (5).

FIG. 8 shows a further embodiment of an adhesive wound dressing of the present invention which comprises a flexible adhesive sheet (22) which comprises a flexible film (23) having on one surface thereof an adhesive layer (24) which adhesive layer is covered by a protector (25) which extends beyond the edges of the flexible adhesive film on at least two opposite edges. A handle (26) comprising a handle portion (27) and an adhesive tape (28) is shown on two opposite edges of the flexible film. The handle comprises a non-adhesive carrying handle portion (27) which is placed abutting the flexible film and an adhesive tape (28) which is used to attach the non-adhesive handle portion to the flexible film. Both the handle portion and the adhesive tape may be coloured in a distinctive colour for example green. The adhesive tape carries a line of perforations (29) which extend over the length of the handle and enable the handle to be separated from the adhesive flexible film without disturbing the flexible film.

FIG. 9 shows an alternative embodiment to that shown in FIG. 8 in that instead of abutting the flexible film, the handle portion is placed a distance from the edge of the flexible film. The perforation line (29) is likewise placed away from the edge of the flexible film so that that when the handle portion is removed along the perforation line a short width of adhesive coated handle remains and may be adhered to the skin of the patient. Again the handle is removed without disturbing the flexible film wound dressing.

Figure 10:
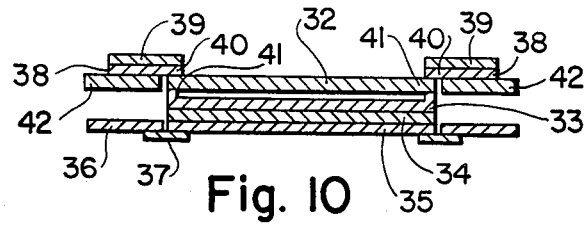
FIGS. 10 to 12 show cross-sections through alternate embodiments of adhesive wound dressings of the present invention in which tearable handles are used in combination with dressings described in European Patent Application No. 107315.

FIG. 10 shows an adhesive wound dressing (31) which comprises a layer of hydrophilic polyurethane (32) sealed around its edges to a film of styrene-butadiene-styrene polymer (33) which has been made water transmitting by cutting slits through it. On one surface this apertured film has an adhesive layer (34) covered by a protector (35) which has been extended by strips (36) attached by means of adhesive coated tabs (37). The tearable handles comprise adhesive coated (38) fibrillated film (39). The edge margin (40) of the handles is adhered to the edge margin of the hydrophilic polyurethane film (41). The remainder of the adhesive on the handles is covered by a protector (42).

Figure 11:
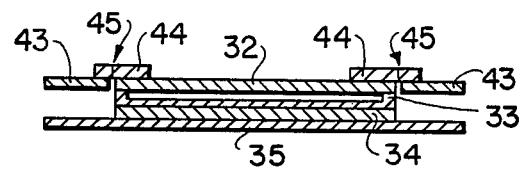

FIG. 11 shows an adhesive wound dressing in which the handles comprise a non-adhesive coated handle portion (43) which is placed abutting the hydrophilic polyurethane film and is attached to it by means of an adhesive coated tape (44). The tape has a line of perforations (45) positioned above the joint of the handle portion and the hydrophilic polyurethane film so that the handle may be removed by tearing along the perforated line without disturbing the wound dressing.

Figure 12:
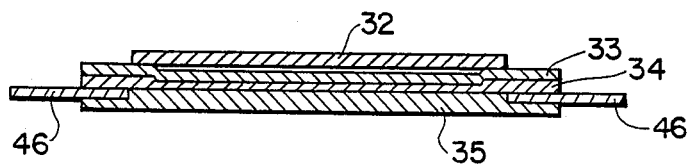

FIG. 12 shows an adhesive wound dressing in which the handles (46) are non-adhesive and are attached to the dressing by means of the adhesive on the water transmitting film.

The adhesive wound dressings shown in the drawings can be applied to a patient by holding the adhesive sheet by means of the handles, removing the protector from the adhesive coating and adhering the adhesive sheet over the wound site. The handles may then be left or torn from the edges of the dressing or when the handles are adhesive coated the protector may be removed from the adhesive layer and the handles adhered to the skin of the patient, in each case to provide a dressing which is completely adhered to the patient without non-adhesive or ragged edges.

In a further aspect the invention provides a method for treating a wound using the adhesive wound dressing of the invention which comprises removing the protector from the adhesive coating, adhering the flexible adhesive coated sheet to the skin surrounding the wound and removing a portion of the handle by tearing along the length of the handle without tearing through the adhesive coated sheet material.

In a second further aspect the invention provides a method for treating a wound using the adhesive wound dressing of the invention which comprises removing the protector from the adhesive coating, adhering the flexible adhesive coated sheet to the skin surrounding the wound, removing the protector from the adhesive coated handle and adhering to the handle, to the skin.

Alternatively the adhesive wound dressings which have adhesive handles can be applied to a patient by first removing the protector strip from one of the handles and adhering it in the required position on the skin to form an anchor point for the dressing. The protector is then removed from the adhesive surface of the wound dressing layer and using the other handle, it can be manoeuvred into its required position. When the dressing is adhered to the skin the remaining handle may be adhered to the skin or torn off. The handle which provided the anchor point may similarly be left in position or removed by tearing. The dressing when applied is not subject to tension found when applying prior art dressings and is therefore more comfortable and does not buckle or crease when the tension is released as the patient moves.

In a further aspect therefore the invention provides a method for treating a wound using the adhesive wound dressing of the invention which comprises removing the protector from one of the adhesive coated handles and adhering it to the skin, peeling off the protector from the adhesive coating of the wound dressing adhering flexible, adhesive coated sheet to the skin surrounding the wound removing the protector from the second handle and adhering it to the skin.

EXAMPLE 1

Preparation of Adhesive Wound Dressing with Adhesive Handles (a) A flexible elastomeric film of polyurethane was formed by dissolving a polyether polyurethane (Estane 5714F, Trade mark, available from B.F. Goodrich Co.) in tetra hydrofuran at 20% solids and casting onto the non-siliconised side of a silicone coated release paper (Steralease 15, Trade mark). Removal of the solvent gave a film which was 30 microns thick. This film was in turn coated with a layer of a polyvinyl ethyl ether pressure sensitive adhesive (adhesive composition A of British Patent No. 1280631). The adhesive layer was 30 microns thick. The polyurethane and adhesive were then transferred to the other side of the release paper in a conventional manner and the three layers slit to give a strip 10 cm wide, which is a suitable size for a wound dressing. The adhesive layer now in contact with the siliconised surface of the release paper.

(b) A siliconised release paper was coated on its silicone coated side with polyvinyl ethyl ether adhesive to give a film which was 30 microns thick. When the film of adhesive had been formed and the solvent removed the adhesive was laminated to a fibrillated thermoplastic film material formed by the method described in British Patent No. 1531715. This laminate which forms the handles of the adhesive dressing was slit to give a strip 2.0 cm wide.

(c) A siliconised release paper was coated on its non-siliconised side with a polyvinyl ethyl ether adhesive and cut into a strip 1 cm wide.

(d) A siliconised release paper was slit to give a strip 2 cm wide.

The adhesive wound dressing shown in FIG. 2 was then assembled as follows: the release paper of (d) is placed adjacent to the release paper of the laminate formed in (a) and the strip of tape formed in (c) used to join the two release papers together. This provides the handles for the protector.

The release paper of the laminate formed in (b) is placed adjacent to the polyurethane film of the laminate formed in (a) and the adhesive coated fibrillated film material formed in (b) moved sideways so that the adhesive edge margin of the fibrillated film material is attached to the edge margin of the poly rethane film. The remainder of the adhesive surface of the fibrillated film material is covered by the release paper. A similar handle portion may be attached in a similar manner to the opposite edge of the polyurethane film.

The strip so formed may be cut across its width to provide a wound dressing which may then be placed in a conventional bacteria proof package, sealed and sterilised either by ethylene oxide or gamma irradiation.

In use the dressing is removed from its package, the protector peeled off and the handles used to position the dressing at the appropriate site. The handles may then be detached, left with the protector in place or the protector removed from the handles and the handles adhered to the skin.

EXAMPLE 2

A dressing was prepared in a similar manner to that described in Example 1 except that only one handle was placed at the edge of the adhesive coated polyurethane film.

This dressing is particularly useful as a dressing for intravenous sites.

EXAMPLE 3

An adhesive coated flexible sheet in which the adhesive surface is covered by a protector is formed in a similar manner to that described in (a) of Example 1.

A siliconised release paper is coated as a strip approximately 0.25 cm wide with a polyvinyl ethyl ether adhesive, to give a film approximately 30 micron thick. This strip is then transfer coated to an edge margin of fibrillated thermoplastic film material formed by the process described in British Patent No. 1531715. The adhesive strip is then used to adhere the handle material to the edge margin of non-adhesive surface the flexible sheet.

The resultant strip may be cut across its width to provide rectangular dressings.

The dressings may be placed in bacteria proof pouches sealed and sterilised by gamma irradiation or ethylene oxide.

EXAMPLE 4

A dressing was prepared by a similar method to that described in Example 1 except that the fibrillated thermoplastic film was replaced by a melt embossed film which had been embossed by means of grooves on each surface of the film which provided a preferred direction of tear which enabled the handles to be removed.

This dressing was packed and sterilised in a conventional manner.

EXAMPLE 5

A dressing was prepared by a similar method to that described in Example 1 except that the handles were formed from a paper which was finger tearable.

EXAMPLE 6

A dressing was prepared by a similar method to that described in Example 1 except that the handles were formed from a 150 micron thick film of polyvinyl chloride which was microporous (Porvic, Trade mark). The adhesive used to coat the handles was in the form of a pattern spread formed by the method described in British Patent No. 815635.

This dressing may be packed and sterilised in a conventional manner.

EXAMPLE 7

A dressing was formed by a similar manner to that described in Example 1 except that the handles were formed from a spun bonded polyester non-woven fabric (Sontara, Trade mark available from Du Pont de Nemours).

EXAMPLE 8

A dressing was formed by a similar method to that described in Example 1 except that the flexible backing sheet was formed from a 32 micron thick film of an elastomer polyether polyester, Hytrel 4056.

The dressing was packed in a bacteria proof pack and sterilised in by gamma irradiation or by ethylene oxide.

EXAMPLE 9

An adhesive coated flexible sheet in which the adhesive surface is covered by a protector is formed in a similar manner to that described in (a) of Example 1 except that the protector extends beyond the edges the adhesive flexible sheet which are to be attached to the handles.

A film of polyester (Melinex, Trade mark), to form the handle portion, is laid on the protector extension and abuts the flexible sheet. A strip of perforated, adhesive coated sheet is then placed on top of the margin of the flexible sheet and of the polyester film handle portion so that the perforated line lies above the gap between the sheet and the film. The strip thus attaches the sheet and the polyester film and with the polyester film forms a handle which is removable by tearing along the perforations so that neither the flexible sheet nor the polyester film is disturbed.

The dressings when cut to the correct size may be placed in bacteria proof pouches, sealed and sterilised.

In use a dressing is removed from its pouch, the protector removed from the adhesive surface of the flexible sheet and the non-adhesive handle portion used to position and place the dressing at the correct site. The handles may then be removed by tearing along the perforated line, so that neither the flexible sheet nor the handle portion is actually torn through.

EXAMPLE 10

(a) An adhesive coated flexible sheet in which the adhesive surface is covered by a protector was formed in a similar manner to that described in (a) of Example 1.

(b) A siliconised release paper was coated on its silicone-coated surface with a polyvinyl ethyl ether adhesive to give a film which was 30 microns thick. When the film of adhesive had been formed and the solvent removed the adhesive was laminated to a fibrillated thermoplastic film material formed by the process described on British Patent No. 1531715. This laminate was slit to give a strip 4.0 cm wide.

(c) A siliconised release paper was coated on its non-siliconised side with a polyvinyl ethyl ether adhesive and cut into a strip 1 cm wide.

(d) A siliconised release paper was slit to give a strip 2 cm wide.

To prepare the dressing the release paper of (d) is placed adjacent to the release paper of the laminate formed in (a) and the strip of tape formed in (c) used to join the two release papers together. This is done on just one edge of the laminate of (a) and forms a handle for the protector.

At the same edge of the laminate of (a), the release paper of the laminate formed in (b) is placed adjacent to the polyurethane film and the adhesive coated fibrillated film material of (b) moved sideways so that the adhesive edge margin of the fibrillated film material is attached to the edge margin of the polyurethane film. The remainder of the adhesive surface of the fibrillated film material is thus covered by the release paper. On the opposite edge of the laminate of (a) a handle was not added to the protector. The adhesive coated fibrillated film material was moved sideways as previously. The protector which covered the adhesive coated fibrillated film material was also moved sideways so as to overlap onto the protector covering the flexible sheet material. The remainder of this protector covers the adhesive surface of the fibrillated film.

The strip so formed may be cut across its width to provide a wound dressing which may then be placed in a conventional bacteria proof package, sealed and sterilised.

In use the dressing is removed from its package, the protector which covers the adhesive on the handle and overlaps onto the protector of the flexible adhesive sheet is removed and the handle adhered in the required position on the skin. Using this as an anchor point, the protector is removed from the flexible adhesive sheet using the protector handle at the opposite edge and the dressing is then adhered to the skin using the remaining handle to provide support during this operation. In this way the dressing is applied without use of excessive tension and avoids the risk of contamination by aseptic contact of the exposed adhesive surface with a person applying the dressing. The handle may be removed by tearing or may be adhered to the skin.

EXAMPLE 11

An adhesive dressing was formed by the method described in Example 5 of European Patent Application No. 107915 in which the continuous layer was formed from a hydrophilic polyurethane which would contain 25% by weight of water, and the water transmitting film comprised a styrene-butadiene-styrene block copolymer (Kraton 1101, Trade mark) with an adhesive coating of an acrylic ester copolymer described in European Patent Application No. 39599 covered by a silicone release paper. The Kraton film, adhesive and protector were apertured by means of a plurality of slits.

A tearable handle was prepared and attached to the surface of the hydrophilic polyurethane remote from the water transmitting film in a similar manner to that described in Example 10.

The dressing may be sealed in a bacteria proof pouch and sterilised in the usual way.

EXAMPLE 12

A dressing was formed in a similar manner to that described in Example 11 except that a layer of a non-woven fabric in the form of a spun-bonded polypropylene (Novelin, Trade mark) was present between the hydrophilic polyurethane and the Kraton film layers.

What we claim is:

1. An adhesive wound dressing which comprises a flexible polymer film having an adhesive surface and a non-adhesive surface on the opposite side thereof, a detachable handle at an edge of the film to facilitate handling of said film and a removable protector over the adhesive surface of the film, in which the handle is adhered along an edge margin of the flexible polymer film and in which the handle is formed from a tearable material to allow a portion of the handle to be detached from the film.

2. An adhesive dressing according to claim 1 in which the detachable handle is coated on one surface with an adhesive and is adhered along an edge margin to an edge margin of the flexible polymer film, the remaining area of adhesive of the handle being covered by a removable protector.

3. An adhesive dressing according to claim 1 in which there is a handle at each of two opoosite sides of the flexible film which film is an elastomeric polymer.

4. An adhesive dressing according to claim 1 in which the flexible film is a moisture vapour permeable polyurethane film which has a thickness of from 10 to 50 microns.

5. An adhesive dressing according to claim 1 in which the handle comprises an integral net formed by the fibrillation of a thermoplastic, embossed film.

6. An adhesive dressing according to claim 2 in which the adhesive coated handle has a moisture vapour permeability of at least $300 \text{gm}^{-2} 24\text{h}^{-1}$ at 37° C. and 100% to 10% relative humidity difference whereby the handle may be adhered to the skin.

7. An adhesive dressing according to claim 2 in which the adhesive on the handle is an acrylate ester copolymer pressure sensitive adhesive.

8. An adhesive dressing according to claim 1 in which the composite strip formed by adhering the edge margin of the handle to the edge margin of the flexible film has a moisture vapour permeability of at least $300 \text{gm}^{-2} 24\text{h}^{-1}$ at 37° C. and 100% to 10% relative humidity difference.

9. An adhesive dressing according to claim 1 in which the handle comprises an adhesive tape having a line of perforations along its length whereby the adhesive tape is placed over an edge portion of the flexible film and at least an edge portion of the handle portion with the line of perforations over the joint between the flexible film and the handle portion so that by tearing along the perforations the handle portion may be detached from the flexible film.

10. An adhesive dressing according to claim 1 in which the handle is from 1.0 to 4.0 cm in width.

11. An adhesive wound dressing comprising a continuous film which has a moisture vapour permeability which is greater when in contact with water than when not in contact with water and which film is attached to a water transmitting film so as to form a sealed portion into which exudate may pass from an exuding wound, said water transmitting layer being interrupted in at least the area within the sealed portion and which water transmitting layer comprises a backing layer and an adhesive layer on the side remote from the continuous film which is suitable for adhering the dressing to the skin, a removable protector over the adhesive layer of the water transmitting layer characterised in that a detachable handle is adhered along an edge margin to an edge margin of the continuous moisture vapour permeable film and which handle is formed from a tearable material to allow a portion of the handle to be detached from the film.

12. An adhesive dressing according to claim 11 in which the handle has an adhesive coating.

13. An adhesive dressing according to claim 11 in which there are two handles adhered to opposite sides of the dressing.

14. An adhesive dressing according to claim 1 in which the dressing is sterile and packaged in a bacteria proof pack.

15. A method of treating a wound using an adhesive wound dressing, which dressing comprises a flexible polymer film having an adhesive surface and a non-adhesive surface on the opposite side thereof, a removable protector over the adhesive surface and a handle formed from tearable material adhered along an edge margin of the flexible polymer film, which method comprises removing the protector from the adhesive coating, adhering the flexible polymer film to the skin surrounding the wound and removing a portion of the handle by tearing along the length of the handle without tearing through the adhesive coated flexible polymer film.

16. A method of treating a wound according to claim 15 in which the adhesive wound dressing has a handle having an adhesive surface which is covered by a protector and which method includes adhering the remaining portion of the handle not removed by tearing, to the skin.

17. A method of treating a wound according to claim 16 in which the method includes removing the protector from the adhesive surface of the handle and adhering the handle to the skin.

18. A method of treating a wound according to claim 15 in which the adhesive wound dressing has a handle at each of two opposite sides of the dressing and the method includes removing a portion of both handles.

19. A method according to claim 15 in which the wound is an indwelling intravenous catheter site.

* * * * *